US005860418A

United States Patent [19]

Lundberg

[11] Patent Number: 5,860,418

[45] Date of Patent: Jan. 19, 1999

[54] METHOD AND AN ARRANGEMENT FOR CHECKING THE OPERATION OF BREATHING EQUIPMENT

[75] Inventor: Mats Erik Lundberg, Jupitervägen, Sweden

[73] Assignee: Comasec International S.A., Saint Denis, France

[21] Appl. No.: 785,039

[22] Filed: Jan. 17, 1997

Related U.S. Application Data

[63] Continuation of Ser. No. 353,273, Dec. 5, 1994, abandoned.

[30] Foreign Application Priority Data

Jul. 28, 1994 [SE] Sweden .................................. 94 02594

[51] Int. Cl.[6] .................................................. A61M 16/00

[52] U.S. Cl. .............................. 128/202.22; 128/205.23; 128/201.27; 128/201.28; 128/204.18; 128/204.21; 128/204.23

[58] Field of Search ......................... 128/204.22, 201.27, 128/202.22, 205.11, 205.23, 201.28, 204.18, 204.21–204.23, 204.26

[56] References Cited

U.S. PATENT DOCUMENTS

| | | | |
|---|---|---|---|
| 2,484,217 | 10/1949 | Gardenier | 128/202.22 |
| 3,224,409 | 12/1965 | Fenger et al. | 128/202.22 |
| 3,478,740 | 11/1969 | Wennberg | 128/202.22 |
| 3,870,012 | 3/1975 | Metivier | 128/202.22 |
| 3,957,044 | 5/1976 | Fletcher et al. | 128/202.22 |
| 4,474,175 | 10/1984 | Hudimac | 128/202.22 |
| 4,674,492 | 6/1987 | Niemyer | 128/202.22 |
| 4,766,894 | 8/1988 | Legrand et al. | 128/202.22 |
| 4,846,166 | 7/1989 | Willeke | 128/202.22 |
| 5,033,818 | 7/1991 | Barr | 128/202.22 |
| 5,097,826 | 3/1992 | Gray et al. . | |
| 5,313,937 | 5/1994 | Zdrojkowski | 128/202.22 |
| 5,392,771 | 2/1995 | Mock et al. | 128/202.22 |
| 5,438,320 | 8/1995 | Taylor | 128/202.22 |
| 5,503,145 | 4/1996 | Clough | 128/202.22 |

FOREIGN PATENT DOCUMENTS

| | | |
|---|---|---|
| 0 324 259 | 7/1989 | European Pat. Off. . |
| 88/06549 | 4/1988 | WIPO . |

*Primary Examiner*—John G. Weiss
*Assistant Examiner*—William J. Deane, Jr.
*Attorney, Agent, or Firm*—Pollock, Vande Sande & Amernick

[57] ABSTRACT

A method of verifying function and status of breathing equipment, wherein the breathing equipment includes a gas supply, a closure valve on the gas supply, a primary pressure regulator downstream of the closure valve, a pressure sensor, a secondary pressure regulator downstream of the primary pressure regulator, a breathing mask downstream of the secondary pressure regulator, an indicator, a processor connected to the pressure sensor and the indicator, and gas lines between the gas supply, the primary pressure regulator, the secondary pressure regulator, and the mask. A processor for receiving sensed data, comparing the sensed data to control values, and producing an output signal is activated. At least one functional or status variable within the equipment is measured. The at least one measured value is compared to a corresponding control value with the processor. An output signal based upon the comparison is produced. The output signal is transmitted to an indicator to indicate whether the at least one measured value substantially corresponds to the at least one control value.

22 Claims, 1 Drawing Sheet

METHOD AND AN ARRANGEMENT FOR CHECKING THE OPERATION OF BREATHING EQUIPMENT

This application is a continuation of U.S. patent application Ser. No. 08/353,273, filed Dec. 5, 1994 now abandoned.

FIELD OF THE INVENTION

The present invention relates to a method of checking the working and/or the operational state of breathing equipment prior to its use, and also to breathing equipment that includes an arrangement for checking at least one working or state parameter of the equipment.

BACKGROUND OF THE INVENTION

It is absolutely necessary to ensure that the breathing equipment used by a diver or a firefighter, for instance, is fully serviceable and faultless prior to entering non-breathable atmospheres, for instance when diving or when working in smoke-filled or toxic environment.

Among other things, it is necessary to check that the system gas-supply is completely full and, therewith, contains the amount of breathing gas that can be expected to be consumed, that the hoses leading to the breathing mask are tightly sealed, that is, will not leak to the surroundings and, therewith, reduce the amount of gas available for breathing, that gas is able to flow from the gas reservoir freely and without hinder and will arrive at the breathing mask in sufficient volumes, that is, that there is practically no resistance to the air flow and that the pressure prevailing in the breathing mask is higher than ambient pressure.

The gas reservoir carried by the person concerned will normally have the form of a gas cylinder that contains breathing gas at a pressure of normally 300 bars, when the cylinder is full. The breathing gas is normally air, although under special circumstances may often contain at least 20 percent by volume oxygen and an inert gas, most often nitrogen and perhaps also helium. In some cases, for instance, for diving to great depths, the breathing gas contains less than 20 percent oxygen by volume. Since the gas reservoir has a relatively small volume, it is important that the reservoir pressure is sufficiently high to supply the user with an anticipated maximum gas volume.

It is also important that the hoses or lines leading from the gas reservoir are tight and that the flow resistance presented thereby is sufficiently small for the gas reservoir to deliver to the user a quantity of gas that is large enough to satisfy the user's requirements, even in the case of an extreme need.

Another important safety problem concerns the gas pressure in the mask when the mask is in place. The mask pressure must be greater than the ambient pressure, so that non-breathable atmosphere, particularly toxic atmosphere, is unable to penetrate into the mask.

SUMMARY OF THE INVENTION

One object of the present invention is to provide a method whereby the above-described functions and/or states can be checked prior to using breathing equipment.

Another object of the invention is to provide an arrangement that permits at least one functional parameter or state parameter of breathing equipment to be checked prior to use.

The first of these methods is achieved in accordance with the invention with a method that is characterized by activating a control circuit that measures at least one functional parameter or state parameter, comparing the measured parameter value with a control value and indicating acceptable or insufficient values, respectively, when the set criterion is fulfilled or when it is not fulfilled.

The second object is achieved with an arrangement that includes breathing equipment, a programmed microprocessor, a sensor that is included in the breathing equipment and connected to the microprocessor, and an indicating arrangement connected to the microprocessor.

According to the present invention, the control circuit is activated either by sensing intermittently a functional parameter or a state parameter of the breathing equipment, comparing the sensed parameter value with the latest measured parameter value, and activating the control circuit when there is a significant difference between these values. Another method to activate the control circuit is to intermittently sense a functional parameter or a state parameter of the breathing equipment, to compare the sensed parameter value with a predetermined value, for example, 10 percent, of the maximum value of the parameter and to activate the control circuit when the sensed parameter is equal to or greater then the predetermined value. Alternatively, the control circuit is activated manually, by pressing a start button, for instance.

BRIEF DESCRIPTION OF THE DRAWINGS

The present invention will now be described in more detail with reference to the accompanying drawing, in which.

DETAILED DESCRIPTION OF THE INVENTION

Figure 1:
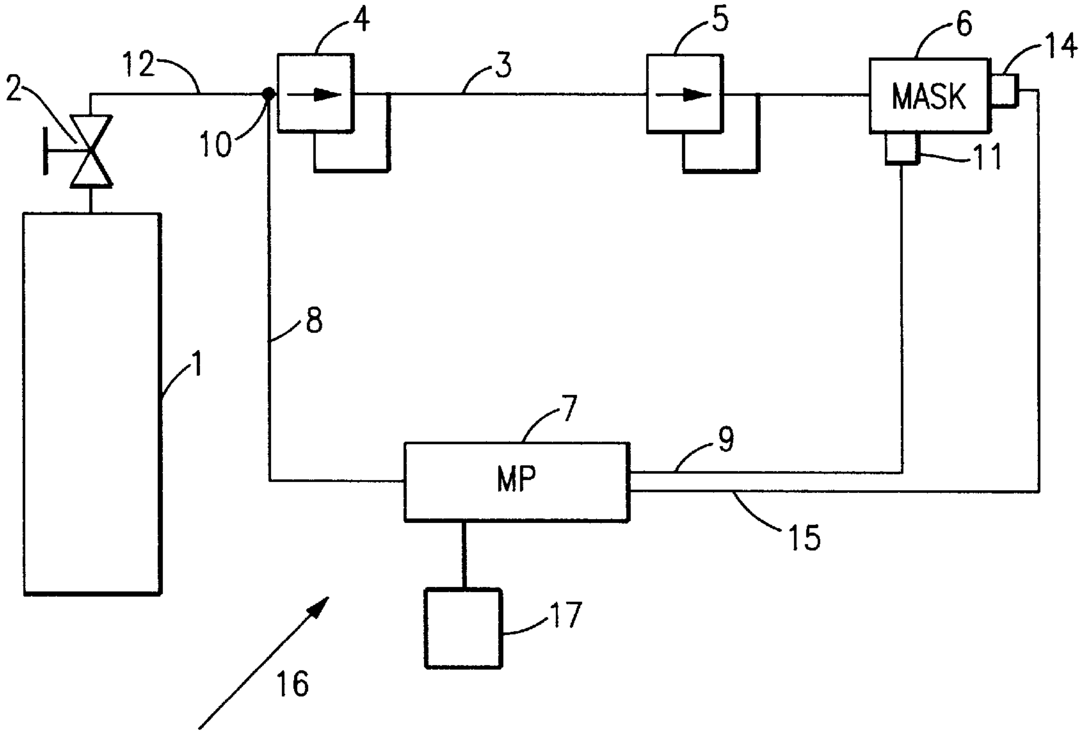
FIG. 1 is a block schematic illustrating breathing equipment provided with a control circuit for carrying out a functional test.

The breathing equipment 16 includes a gas reservoir, which is usually a gas cylinder or gas container 1 containing breathing gas. The breathing gas may include, for instance, air or an oxygen-containing gas that includes, most frequently, at least 20 percent by volume oxygen and an inert gas, for instance nitrogen or helium, at a pressure of normally 300 bars when the container is completely full. The gas container 1 includes an outlet opening in which there is mounted a closure valve 2. The gas container 1 is connected to a primary pressure regulator 4, through the medium of the closure valve 2. A line 3 extends from the primary pressure regulator 4 to a secondary pressure regulator 5 which is located immediately upstream of a breathing mask 6.

The pressure regulator 4 is set to reduce the pressure in the gas container 1 to typically about 7 bars in the line 3 downstream of the primary pressure regulator, that is, the first regulator 4. The second pressure regulator 5 is set to reduce the pressure of the gas passing to the breathing mask 6 still further, to a pressure of about 25 mm water column, that is, to a pressure suitable for use in the mask 6. As the wearer breathes, the pressure in the mask will oscillate around this value during a breathing phase, therewith constantly maintaining an overpressure. The pressure regulator 5 is normally a requirement-controlled regulator that is closed prior to putting on the mask 6 and is opened by the subpressure that is generated when the wearer first inhales. The regulator 5 is opened when the relative pressure in the mask 6 falls beneath a preset value. It is necessary to activate other similar regulators manually, through separate activating means.

A pressure sensor 10 is mounted in a space 12 formed between the closure valve and the primary pressure regulator 4. This sensor 10 measures the pressure in the space 12 and is connected to a microprocessor 7 by means of a line 8. Line 9 extends from the microprocessor 7 to an indicating arrangement 11 that is preferably, but not necessarily, mounted in the breathing mask 6. The indicating arrangement 11 includes at least one indicating device. Preferably, at least one indicating device is provided for each function included in the functional test. The indicating device is preferably a light-emitting diode (LED). The indicating arrangement 11 provided in the breathing mask 6 is preferably visible to the user, both when the mask 6 is worn and when removed, and will also be visible to people in the vicinity of the user.

The breathing mask 6 included in the breathing equipment is preferably also provided with a differential pressure meter 14, which is connected to the microprocessor 7 by means of a line 15. The measured differential pressure is indicated in an indicating device by the indicating arrangement 11. Accordingly, the mask 6 of the illustrated breathing equipment is provided with a differential pressure meter 14 that is connected to microprocessor 7 by a line 15. The measured differential pressure is indicated in the indicating arrangement 11 and is visible to the user with the mask 6 fitted.

According to the present invention, the lines 9 and 15 may be replaced with cordless connections between the microprocessor 7 and the indicating arrangement 11 and between the microprocessor and the differential pressure meter 14, respectively.

The microprocessor 7 is programmed to carry out some or all of the functions described below. According to a third embodiment, the microprocessor senses the pressure in the space 12 intermittently, for instance every second or at some other chosen frequency, through the medium of the sensor 10, and compares the sensed pressure with the pressure that was last sensed. Alternatively, the microprocessor senses the pressure in the space 12 intermittently, for instance every second or at some other chosen frequency, through the medium of the sensor 10, and compares the sensed pressure value with a predetermined pressure value, for example 10 percent of the maximum pressure in the gas container 1.

According to the invention, before testing the breathing equipment, the closure valve 2 is opened to an extent that the space 12 is under the same pressure as the container 1, whereafter the valve 2 is closed. The pressure in the space 12 increases as gas from the container 1 flows into the space. As the valve 2 is opened, the sensor 10 will deliver a much higher pressure value to the microprocessor 7 as the pressure increases than before the pressure increase. The microprocessor 7 receives the start signal required to carry out the functional diagnosis and status diagnosis in accordance with the invention in conjunction with the pressure comparison that automatically takes place.

According to another embodiment, the microprocessor is fitted with a start button that replaces the start signal obtained when a marked pressure increase is obtained after each alternate sensed pressure value when the closure valve 2 is opened. It is also necessary in this case to open the closure valve to an extent that the pressure in the space 12 will at least substantially equal the gas pressure in the container 1, whereafter the valve is closed.

In order for the test to provide the information required, it is necessary for the primary pressure valve included in primary pressure regulator 4 to be set so that a suitable pressure will be obtained in the line 3. Furthermore, the secondary pressure regulator 5 must be closed prior to opening the valve 2.

Figure 2:
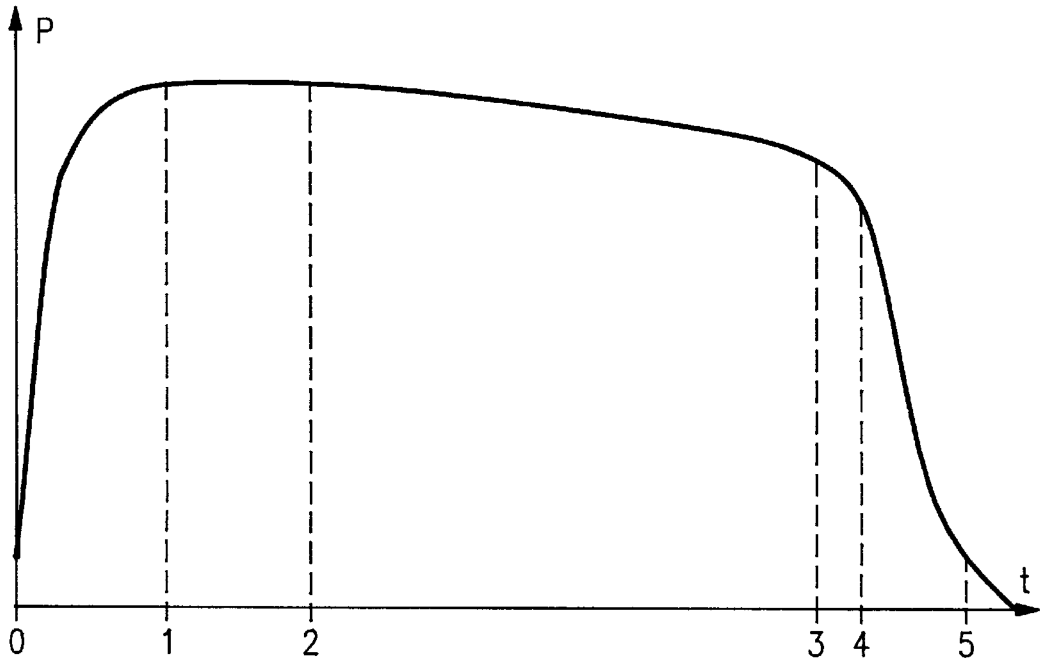
FIG. 2 is a diagram that illustrates primary pressure as a function of time when carrying out a functional test.

FIG. 2 illustrates the gas pressure in the proximity of the sensor 10 as a function of the time at which the test was carried out. None of the axes is graduated. Position 0 shows the relative pressure at the sensor 10 prior to starting the test. When the closure valve 2 is opened, the pressure in the space 12 will rise to the pressure of the gas reservoir, as illustrated at position 1, and there is obtained in the line 3 a pressure that is contingent on the setting of the regulator 4, this pressure being 7 bars in the illustrated case. The valve 2 is then closed. The pressure that now prevails in the line 3 is not shown in FIG. 2.

The microprocessor 7 senses the pressure prevailing in the space 12 after a maximum pressure has been reached, that is, after position 1, for instance at position 2. If the pressure is below a first control value, for instance a value within the range of 97 to 80 percent, particularly a value in the vicinity of 90%, for instance a value in the range of 95% to 85%, particularly about 90% of the full pressure in the gas reservoir 1, the microprocessor will understand this to mean that the gas supply does not fulfill the necessary pressure criterion and indicate in the indicating arrangement 11 an insufficiency value. The indicating arrangement preferably is mounted in the mask 66. The indicating arrangement 11 indicates an acceptable value, when the pressure exceeds or is equal to the control value.

The present functional test also includes ensuring that the line leading to the mask 6, that is, the second pressure regulator 5, is tight and will not leak gas to the surroundings. To this end, the sensor 10 measures the pressure after a predetermined time period, for instance 3–20 seconds, from the time at which pressure was measured in position 2 in FIG. 2. The duration of this time lapse will depend on the level of accuracy desired. This pressure is measured before position 3. When the pressure difference between the pressure measured at position 2 and the pressure measured before position 3 is greater than a second control value, the indicating arrangement 11 will indicate an insufficiency value. When the pressure difference is lower than or equal to the control value, the indicating arrangement will indicate that the value is acceptable.

After testing the equipment for tightness, that is, leakage, a check is made to ensure t hat the line 3 to the mask 6 is not blocked or that the supply of gas to the mask 6 through the regulator 5 is not hindered in some other way. To this end, the regulator 5 is opened with the mask 6 removed, so that the gas present between the closure valve 2 and the regulator 5 is able to flow freely to the atmosphere, the valve 2 still being closed. Then, the pressure decrease in the space 12 is measured as a function of time, with the aid of the sensor 10.

One criterion of acceptable outflow or function is found in the time taken for the pressure to fall to a% of the original pressure, for instance the pressure that prevailed prior to opening the second regulator, from (b–a)%, where b is a value greater than a and equal or less than 100, for example 50, and a may be 10 for instance. When this time duration is equal to or smaller than a third control value, the indicating arrangement 11 will indicate an acceptable value; in other cases, an unacceptable value will be indicated.

This is shown in FIG. 2, where position 3 indicates that the second regulator 5 is open so that the gas content of the equipment downstream of the closure valve is able to flow freely from the system. Position 4 indicates that the pressure has fallen to a value of (100–a)% of the pressure prevailing at position 3. Position 5 indicates that the pressure has fallen to a%. When the time, $t_5$–$t_4$, is shorter than or equal to the third control value, the function of the equipment with regard to gas supply is considered to be fully acceptable.

Another criterion for acceptable gas outflow, or function, is one in which the pressure that prevails after opening the second regulator 5 is measured after a predetermined time interval. If, when measured, it is found that the pressure has fallen to the same value as a predetermined highest value or to a lower value, during this time period, the microprocessor 7 will indicate, via the indicating arrangement 11, that the supply of gas to the mask 6 is acceptable. Otherwise, the indicating arrangement 11 will indicate that the equipment is faulty.

This second criterion is also shown in FIG. 2. In this case, the pressure is measured from the time of opening the second regulator 5, that is, at position 3, and is compared with a fourth control value, for instance at position 5 for the sake of simplicity. If the pressure at time point $t_5$ exceeds a predetermined pressure, p5, the ordinate at position 5, the indicating arrangement 11 will indicate a malfunction.

Naturally, the pressure decrease as a function of time can be measured in other ways. For instance, the derivative of the pressure curve can be measured as a function of time at the curve inflection point. The derivative, that is, the directional coefficient of the curve, is then a measurement of the outflow rate.

Another important function of the equipment resides in checking that the control circuit (10, 7, 8, 9, 11) works satisfactorily. Accordingly, the indicating arrangement 11 will indicate the functional state of the control circuit (10, 7, 8, 9, 11) when measuring the pressure after having changed the pressure in the region where the sensor 10 acts. A malfunction is indicated if this does not take place.

Another important function of the present invention is that the face mask 6 fits tightly to the user's face and that when breathing with the closure valve 2 open a relative overpressure with regard to ambient atmosphere is maintained in the space between the mask 6 and the wearer's face. Accordingly, the closure valve 2 is opened after carrying out the aforedescribed tests, and a check is optionally made to ensure that the primary pressure regulator 4 is set to the correct setting. After having put on the mask 6, the regulator will open automatically as the user breathes in, or is opened manually if the regulator should be closed or switched-off.

The breathing mask 6 includes a sensor 14 that measures the difference between the pressures that prevail inside and outside the mask 6. Should the pressure between the mask 6 and the face of the wearer be greater than the pressure prevailing outside the mask during at least one breathing cycle, the indicating arrangement 11 will indicate a positive pressure, that is, a fully acceptable function. Otherwise, the indicating arrangement will indicate a non-acceptable function. According to one preferred embodiment, serviceable equipment is indicated when all tests have shown an acceptable result. The use of the equipment is prevented when one or more tests show an unacceptable result. However, according to one preferred embodiment, the equipment can be used when the gas reservoir has been filled to a higher pressure than a predetermined lowest pressure, wherein the indicating arrangement 11 will indicate that the reservoir pressure is lower than the lowest recommended value for a full gas reservoir. However, use of the equipment is prevented, or blocked, when the pressure in the gas reservoir is lower than a lowest predetermined pressure value, for instance 20 percent of maximum pressure.

The microprocessor is powered by a small source of electric current, for instance by one or more batteries. The indicating arrangement will also preferably indicate the remaining operational time or useful life of the current source. If the remaining operational time is lower than a predetermined operational time, this is indicated in the indicating arrangement. According to another preferred embodiment, the equipment includes a registering device 17 that is associated with the control circuit. This device registers each activation of the control circuit and the results of the tests and functional checks carried out after each activation. An active or a passive memory unit connected to the microprocessor is one example of such a registering device. This registration enables subsequent checks to be made to ascertain the number of times the equipment has been tested and the results obtained in conjunction therewith.

I claim:

1. A method for verifying the functioning and status of breathing apparatus for an irrespirable environment prior to use of the apparatus, the method comprising the steps of:

providing a breathing apparatus including a gas supply, a closure valve on the gas supply, a pressure regulator downstream of the gas supply, at least one sensor, a breathing mask downstream of the pressure regulator, a status indicator, processing means connected to the sensor and the status indicator, and gas lines between the gas supply, the pressure regulator, and the masks;

prior to use of the breathing apparatus the processing means is activated for receiving sensed data, comparing the sensed data with predetermined control values, and producing an output signal;

measuring at least one functional or status variable within the apparatus;

comparing at least one of the at least one measured variables with a corresponding stored control value in the processing means; and generating an output signal based upon the comparison to verify whether the breathing equipment is usable prior to use.

2. A method according to claim 1, further comprising the steps of:

continuously measuring at least one functional or status variable with in the breathing apparatus during use of the breathing apparatus;

continuously comparing the at least one measured functional or status value to a corresponding predetermined control value for said at least one measured functional or status value with the processing means during use of the breathing apparatus;

continuously producing an output signal based upon the comparison during use of the breathing apparatus;

continuously transmitting the output signal to the status indicator during use of the breathing apparatus; and continuously indicating whether the at least one measured functional or status value substantially corresponds to the at least one predetermined control value for the at least one measured functional or status value during use of the breathing apparatus.

3. A method according to claim 1, further comprising the steps of:

transmitting the output signal to the status indicator; and indicating whether the at least one measured value substantially corresponds to the at least one predetermined control value.

4. A method according to claim 1, wherein said breathing apparatus further comprises means for recording each operation of the apparatus and result of the comparison, said method further comprising the steps of:

transmitting the output signal to the recording means; and registering the operation of the apparatus and result of the comparison with the recording means.

5. A method according to claim 1, wherein said sensor is a pressure sensor and activating the processing means includes the following steps:

closing the pressure regulator;

opening the closure valve thereby creating a gas pressure in the gas lines between the closure valve and the pressure regulator;

measuring the gas pressure with the pressure sensor; and transmitting a signal from the pressure sensor to the processing means thereby activating the processing means.

6. A method according to claim 1, wherein the breathing apparatus further includes an activating switch for activating the processing means and the processing means is activated by moving the activating switch into an activating position.

7. A method according to claim 1, wherein the at least one sensor is a pressure sensor and the at least one functional or status variable includes a gas pressure within the gas line between the closure valve and the pressure regulator, said method further comprising the steps of:

closing the pressure regulator;

opening the closure valve thereby permitting gas to flow into the gas lines between the closure valve and the pressure regulator;

closing the closure valve;

measuring a first gas pressure with the pressure sensor;

comparing the first measured gas pressure to a predetermined control value for the first measured gas pressure; and transmitting a signal to the status indicator to produce an indication whether the first measured gas pressure is within a predetermined acceptable range of the predetermined control value for the first measured gas pressure.

8. A method according to claim 7, wherein the status indicator produces an indication that the first measured gas pressure is within a predetermined acceptable range when the first measured gas pressure is greater than or equal to the predetermined control value for the first measured gas pressure.

9. A method according to claim 7, wherein the status indicator produces an indication that the first measured gas pressure is not within a predetermined acceptable range when the first measured gas pressure is 97–80% of the predetermined control value for the first measured gas pressure.

10. A method according to claim 7, further comprising the steps of:

measuring a second gas pressure with the pressure sensor;

calculating a difference between the first measured gas pressure and the second measured gas pressure;

comparing the difference between the first measured gas pressure and the second measured gas pressure to a predetermined control value for the difference between first measured gas pressure and the second measured gas pressure; and transmitting a signal to the status indicator to produce an indication whether the difference between the first measured gas pressure and the second measured gas pressure is within an acceptable range of the predetermined control value for the difference between first measured gas pressure and the second measured gas pressure.

11. A method according to claim 10, wherein the second measured gas pressure is measured from 3 to 20 seconds after the first measured gas pressure.

12. A method according to claim 1, wherein the at least one sensor is a pressure sensor and the at least one functional or status variable includes a measured decrease in gas pressure as a function of time, said method further comprising the steps of:

closing the pressure regulator;

opening the closure valve thereby permitting gas to flow into the gas lines between the closure valve and the pressure regulator;

closing the closure valve;

measuring a first gas pressure with the pressure sensor;

opening the regulator;

monitoring a decrease in the first measured gas pressure as a function of time with the pressure sensor;

comparing the monitored decrease in the first measured gas pressure as a function of time with a predetermined control value for the decrease in gas pressure as a function of time; and transmitting a signal to the status indicator to produce an indication whether the monitored decrease in gas pressure is within a predetermined acceptable range of the predetermined control value for the decrease in gas pressure as a function of time.

13. A method according to claim 1, wherein the at least one sensor is a pressure sensor and the at least one functional or status variable includes a decrease in gas pressure in the gas lines between the closure valve and the mask during a predetermined time interval, said method further comprising the steps of:

closing the pressure regulator;

opening the closure valve thereby permitting gas to flow into the gas lines between the closure valve and the pressure regulator;

closing the closure valve;

measuring a first gas pressure with the pressure sensor;

opening the pressure regulator;

measuring a second gas with the pressure sensor after the passage of a predetermined time interval;

calculating a difference between the first measured gas pressure and the second measured gas pressure;

comparing the calculated difference in pressure with a predetermined control value for the difference in gas pressure; and transmitting a signal to the status indicator to produce an indication whether the calculated value is within an acceptable range of the predetermined control value for the difference in gas pressure.

14. A method according to claim 1, wherein the at least one sensor is a pressure sensor and the at least one functional or status variable includes a measure of a derivative of a gas flow curve as gas flows out of the gas lines between the closure valve, the pressure regulator and the mask, said method further comprising the steps of:

closing the pressure regulator;

opening the closure valve;

measuring gas pressure with the pressure sensor;

closing said closure valve;

opening said pressure regulator;

monitoring a decrease in the gas pressure as a function of time with the pressure sensor;

calculating the derivative of the gas flow curve as the gas pressure decreases;

comparing the calculated derivative of the gas flow curve with a predetermined control value for the derivative of the gas flow curve; and transmitting a signal to the status indicator to produce an indication whether the calculated derivative of the gas flow curve is within an acceptable range of the predetermined control value for the derivative of the gas flow curve.

15. A method according to claim 1, wherein the at least one sensor is a pressure sensor and the at least one functional or status variable includes a gas pressure within the mask, said method further comprising the steps of:

placing the mask on a wearer's face;

opening the closure valve;

opening the pressure regulator;

measuring a gas pressure within the mask with the pressure sensor;

comparing the measured pressure within the mask to an ambient pressure outside the mask; and transmitting a signal to the status indicator to produce an acceptable indication if the measured pressure within the mask is greater than the ambient pressure.

16. A method according to claim 1, further comprising the step of causing the status indicator to indicate when the processor is activated.

17. A breathing apparatus for an irrespirable environment, comprising:

a supply of breathing gas;

a closure valve on the gas supply;

a pressure regulator downstream of the gas supply;

at least one sensor for sensing at least one functional or status variable within the apparatus;

a breathing mask downstream of the pressure regulator;

an indicator for indicating a status of the breathing apparatus;

at least one gas line interconnecting the gas supply, the pressure regulator, and the mask; and means for verifying functioning and status of the breathing apparatus prior to use of the breathing apparatus comprising processing means connected at least to the at least one sensor and the status indicator;

said verifying means measuring at least one functional or status variable within the apparatus, comparing at least one of the at least one measured variable with a corresponding predetermined reference value in the processor, generating an output signal based upon the comparison to verify whether the breathing equipment is usable prior to use.

18. An apparatus according to claim 17, wherein said status indicator includes at least one light emitting diode and is mounted on said mask and is visible to a wearer of said mask and/or people in the vicinity of the mask.

19. A breathing apparatus according to claim 17, wherein said processing means is a microprocessor and said verifying means transmits the output signal from the processing means to the status indicator and indicates whether the at least one measured value substantially corresponds to the at least one control value.

20. A breathing apparatus according to claim 17, wherein said verifying means further comprises means for recording each operation of the apparatus and result of the comparison, and transmits the output signal to the recording means and registers the operation of the apparatus and result of the comparison with the recording means.

21. A method for verifying the functioning and status of breathing apparatus for an irrespirable environment prior to use of the apparatus, comprising the steps of:

providing a breathing apparatus comprising a supply of breathing gas, a closure valve on the gas supply, a pressure regulator downstream of the gas supply, at least one sensor, a breathing mask downstream of the pressure regulator, a status indicator, processing means connected to the at least one sensor and the status indicator for receiving sensed data related to the pressure of the breathing gas and transmitting a signal corresponding to the status of the breathing apparatus, and gas lines between the gas supply, said pressure regulator, and the mask;

prior to use of the breathing apparatus providing a closed end to the breathing apparatus by closing the pressure regulator or by placing the mask over the face of a user of the breathing apparatus;

opening the closure valve on the gas supply;

sensing data including at least one variable related to a gas pressure within at least a portion of the breathing apparatus, the at least one variable being selected from the group consisting of static pressure of the breathing gas and a change of pressure of the breathing gas with respect to time;

transmitting the sensed data to the processing means;

comparing the at least one measured variable with a corresponding reference value;

producing an output signal based upon the comparison to verify whether the breathing equipment is usable prior to use.

22. A method for verifying the functioning and status of breathing apparatus for an irrespirable environment prior to use of the apparatus, the method comprising the steps of:

providing a breathing apparatus including a gas supply, a closure valve on the gas supply, a first pressure regulator downstream of the gas supply, a pressure sensor arranged between the closure valve and the first pressure regulator, a second pressure regulator downstream of the first pressure regulator, a breathing mask downstream of the first pressure regulator, a status indicator, processing means for receiving sensed data, comparing the sensed data with predetermined control values, and producing an output signal connected to the sensor and the status indicator, and gas lines between the gas supply, the first pressure regulator, the second pressure regulator, and the mask;

prior to use of the breathing apparatus the processing means is activated;

closing at least one of the first pressure regulator and the second pressure regulator;

opening the closure valve thereby permitting gas to flow into the gas lines between the closure valve and the first pressure regulator or the second pressure regulator;

closing the closure valve;

measuring at least one functional or status variable related to a gas pressure within the gas line between the closure valve and the first pressure regulator or the second pressure regulator;

comparing the at least one measured variable with a corresponding predetermined stored control value in the processing means; and transmitting a signal based upon the comparison to the status indicator to produce an indication whether the to verify whether the breathing equipment is usable prior to use.

* * * * *